US009091573B2

(12) United States Patent
Van Der Lee et al.

(10) Patent No.: US 9,091,573 B2
(45) Date of Patent: Jul. 28, 2015

(54) DETERMINING A FLOW CHARACTERISTIC OF AN OBJECT BEING MOVABLE IN AN ELEMENT

(75) Inventors: Alexander Marc Van Der Lee, Vento (NL); Jeroen Veen, Nijmegen (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/117,635

(22) PCT Filed: May 22, 2012

(86) PCT No.: PCT/IB2012/052557
§ 371 (c)(1),
(2), (4) Date: Nov. 14, 2013

(87) PCT Pub. No.: WO2012/164438
PCT Pub. Date: Dec. 6, 2012

(65) Prior Publication Data
US 2014/0085635 A1     Mar. 27, 2014

(30) Foreign Application Priority Data

Jun. 1, 2011 (EP) .................................. 11168498

(51) Int. Cl.
*G01N 21/00*     (2006.01)
*G01F 1/00*     (2006.01)
(Continued)

(52) U.S. Cl.
CPC ................ *G01F 1/00* (2013.01); *A61B 5/0261* (2013.01); *A61B 5/6801* (2013.01); *G01N 21/53* (2013.01);
(Continued)

(58) Field of Classification Search
CPC ................ G01N 21/53; G01N 21/538; G01N 2021/4709; G01N 15/0205; G01N 21/21
USPC ......................................................... 356/342
See application file for complete search history.

(56) References Cited

U.S. PATENT DOCUMENTS 4,611,912 A  9/1986 Falk et al.
4,733,609 A  3/1988 Goodwin et al.
(Continued)

FOREIGN PATENT DOCUMENTS

WO  2009027896 A1  3/2009
WO  2009027898 A1  3/2009

OTHER PUBLICATIONS

Fredriksson, I., et al.; Laser Doppler Flowmetry—A Theoretical Framework; 2007; Dept. of Biomedical Engineering, Linkoping University; 13 pages. www.imt.liu.se/bit/ldf/ldfmain.html.
(Continued)

*Primary Examiner* — Tarifur Chowdhury
*Assistant Examiner* — Md Rahman

(57) ABSTRACT

A sensor device (340) for determining a flow characteristic of an object (341) being movable in an element (342) comprises a light emitting unit (344) configured for emitting light towards the element (342) and a light detecting unit (344) configured for detecting light scattered back from the element (342). The sensor device (340) comprises an optical unit (346) configured for spatially separating a light incidence element portion (348) of the element (342) and a light detection element portion (350) of the element (342) from one another, wherein the light incidence element portion (348) is associated with the emitted light inciding on the element (342) and the light detection element portion (350) is associated with the back-scattered light scattered back from the element (342) for detection. The sensor device (340) comprises a determining unit (358) configured for determining the flow characteristic of the object (341) being movable in the element (342) based on light indicative of the emitted light and the detected back-scattered light. The sensor device (340) allows for an accurate and easy determination of the flow characteristic of the object (341).

20 Claims, 3 Drawing Sheets

(51) Int. Cl.
- *A61B 5/026* (2006.01)
- *A61B 5/00* (2006.01)
- *G01P 3/36* (2006.01)
- *G01P 5/26* (2006.01)
- *G01S 17/58* (2006.01)
- *G01S 17/88* (2006.01)
- *G01S 7/491* (2006.01)
- *G01N 21/53* (2006.01)

(52) U.S. Cl.
CPC . *G01P 3/366* (2013.01); *G01P 5/26* (2013.01); *G01S 7/4916* (2013.01); *G01S 7/4917* (2013.01); *G01S 17/58* (2013.01); *G01S 17/88* (2013.01); *A61B 2562/0233* (2013.01); *A61B 2562/146* (2013.01)

(56) References Cited

U.S. PATENT DOCUMENTS

| | | | |
|---|---|---|---|
| 5,783,836 A * | 7/1998 | Liu et al. | 250/574 |
| 6,411,370 B1 | 6/2002 | Rajchel et al. | |
| 2002/0049389 A1 * | 4/2002 | Abreu | 600/558 |
| 2006/0279747 A1 * | 12/2006 | Tamiya | 356/616 |
| 2007/0030477 A1 * | 2/2007 | Hwang et al. | 356/237.1 |
| 2008/0147147 A1 | 6/2008 | Griffiths et al. | |
| 2010/0033719 A1 * | 2/2010 | Hendriks et al. | 356/317 |
| 2010/0168586 A1 | 7/2010 | Hillman et al. | |
| 2010/0185106 A1 | 7/2010 | Suijver et al. | |

OTHER PUBLICATIONS

Meigas, K., et al.; Self-mixing in a diode laser as a method for cardiovascular diagnostics; 2003; Journal of Biomedical Optics; 8(1)152-160.

Ozdemir, S. K, et al.; Noninvasive blood flow measurement using speckle signals from a self-mixing laser diode: in vitro and in vivo experiments; 2000; Opt. Eng.; 39(9)2574-2580.

Wan, X-J., et al.; Self-mixing Interference in Dual-Polarization Microchip Nd:YAG Lasers; 2004; Chin. Phys. Lett.; 21 (11)2175-2178.

Zhang, Y., et al.; Laser Doppler Velocimetry based on self-mixing effect in vertical-cavity surface-emitting lasers; 2007; IEEE Trans. on Electronic Measurement and Instruments; I-413-I-416.

* cited by examiner

DETERMINING A FLOW CHARACTERISTIC OF AN OBJECT BEING MOVABLE IN AN ELEMENT

FIELD OF THE INVENTION

The invention relates to a sensor device for and a method of determining a flow characteristic of an object being movable in an element.

BACKGROUND OF THE INVENTION

Laser Doppler velocimetry (LDV), which is also referred to by laser Doppler anemometry (LDA) represents a measurement technique for determining a flow characteristics of a movable object using the Doppler effect. In particular, Laser Doppler velocimetry is usable in conjunction with medical diagnosis applications, in order to, for example, determine a flow characteristic of micro vascular blood or tissue perfusion characteristics of a person. In the medical area, LDV is also referred to as laser Doppler flowmetry (LDF). Alternatively, the technique may be used in the area of material machining, in order to determine a flow characteristic of a material particle stream. In the following, reference is made to the medical area without loss of generality.

One LDF based technique for determining the flow characteristic of blood of a person will be explained with reference to FIG. 1. Coherent laser light 102 emitted by a laser unit is incident on a skin portion 104 of a skin 106 of the person. The light 102 comprises a frequency $\omega 0$, as illustrated in a diagram 108 with an ordinate of the diagram 108 representing a frequency (measured in Hertz) and an abscissa of the diagram 108 representing an intensity of the emitted light 102 (measured in arbitrary units). The light 102 penetrates into surface layers of the skin 106 beneath the skin portion 104, and is amongst others scattered at blood cells 108a-e moving in the skin 106. Multiple scattering events of the light 102 at different blood cells 108a-c, e as well as a single scattering event of the light 102 at one blood cell 108d are illustrated in FIG. 1 for illustration purposes. Respective back-scattered light 110a-c propagates subsequent to the scattering event(s) to a detector 112. Reflection of the light 102 at the skin portion 104 on which the light 102 is incident may also cause reflected light 110d to propagate to the detector 112. The detector 112 detects all incoming light 110a-d with the detected light comprising a frequency distribution centered around the frequency $\omega 0$ of the light 102, as illustrated in a diagram 114. An ordinate of the diagram 114 represents a frequency (measured in Hertz) and an abscissa of the diagram 114 represents an intensity of the detected light (measured in arbitrary units).

Ideally, in accordance with the Doppler effect, each of the back-scattered light 110a-c comprises a frequency $\omega 0+\Delta\omega$ with $\Delta\omega$ denoting a frequency shift compared to the initial frequency $\omega 0$ of the light 102. The frequency shift $\Delta\omega$ is determined by a vectored velocity of the respective blood cell(s) 108a-e and the directional change of the incident and scattered light. In the one-dimensional case, a reduction of the distance between a moving blood cell and the laser unit leads to a positive signed frequency shift $\Delta\omega$, while an increase of the distance between a moving blood cell and the light source leads to a negative signed frequency shift $\Delta\omega$. The reflected light 110d ideally comprises the frequency $\omega 0$ of the light 102.

The frequency distribution of the detected light illustrated in the diagram 114 is caused by several effects. Further, a clear frequency shift $\Delta\omega$ may not be observed owing to random velocity values of the blood cells. The blood cells 108a-e may move in all directions and comprising different velocity values, thereby leading to different values of the frequency shifts $\Delta\omega$ of the back-scattered light 110a-c.

The flow characteristic of the blood is then determined based on the obtained frequency spectrum.

Although back-scattered light is predominately illustrated in FIG. 1, the detected light may comprise a high fraction of the reflected light. Thus, the above described measurement technique may comprise low depth sensitivity, and, when considering a small Doppler frequency shift, an accuracy of the determination of the flow characteristic of the blood may be low.

A further option for the determination of the flow characteristic of the blood based on the Doppler effect additionally employs self-mixing interferometry (SMI). A respective SMI-LDF based measurement principle will be explained with reference to FIG. 2. A laser unit 220 emits light 222 towards a skin portion 224 of a skin of a person. A distance between a front side of the laser unit 220 and the skin portion 224 is indicated in FIG. 2 by s. Light 226 reflected or scattered back from the skin portion 224 enters again the laser unit 220. Mixed light 228 is generated in the laser unit 220 in that light in the laser unit which is to be emitted (and thus corresponds to the emitted light 222) and the detected back-scattered and reflected light 226 mix in the laser unit 220. The mixed light 228 is outputted by the laser unit 220, and is detected by a photodiode 230 arranged externally of the laser unit 220. A power spectrum obtained by the photodiode 230 is analyzed using a so called three-mirror Fabry-Perot cavity model with the front surface, now referenced by 232, and a rear surface 234 of the laser unit 220 and the surface 236 of skin portion 224 representing the respective mirrors. A result of the analysis provides information about the flow velocity of the blood in the skin portion 224.

As stated above, the determination of the flow characteristic of the blood based on SMI may also suffer from a poor accuracy.

WO 2009/027896 describes a SMI based method and apparatus for measuring skin properties of a person, for example a dehydration level of the skin. The apparatus comprises a laser sensor configured for transmitting laser light towards the skin portion to be investigated and for receiving laser light reflected from the skin portion. The laser sensor comprises a photodiode configured for measuring power fluctuations of the laser light of the laser sensor, in order to determine a recoil velocity of the skin portion based on a change of the power fluctuation of the laser light over time. Due to the self mixing effect the back-scattered light gives rise to power fluctuation of the laser. A polarizer of the apparatus is arranged between the laser sensor and the skin portion, in order to suppress fractions of the reflected light which comprises a different polarization compared to the emitted light. The skin property is determined based on the power fluctuations.

SUMMARY OF THE INVENTION

It is an object of the present invention to provide a method for accurately and easily determining a flow characteristic of an object being movable in an element. Further, it is an object of the invention to provide a sensor device allowing for accurately and easily determining the flow characteristic of the object being movable in the element.

The object defined above is solved by a sensor device for and a method of determining a flow characteristic of an object being movable in an element according to the independent claims.

According to an exemplary aspect of the invention, a sensor device for determining a flow characteristic of an object being movable in an element is provided, the sensor device comprising a light emitting unit configured for emitting light towards the element, a light detecting unit configured for detecting light scattered back from the element, an optical unit configured for spatially separating a light incidence element portion of the element and a light detection element portion of the element from one another, wherein the light incidence element portion is associated with the emitted light inciding on the element and the light detection element portion is associated with the back-scattered light scattered back from the element for detection, and a determining unit configured for determining the flow characteristic of the object being movable in the element based on light indicative of the emitted light and the detected back-scattered light.

According to another exemplary aspect of the invention, a method of determining a flow characteristic of an object being movable in an element is provided, the method comprising emitting light towards the element by a light emitting unit, detecting light scattered back from the element by a light detecting unit, and determining, by a determining unit, the flow characteristic of the object being movable in the element based on light indicative of the emitted light and the detected back-scattered light, wherein a light incidence element portion of the element and a light detection element portion of the element are spatially separated from one another by an optical unit, wherein the light incidence element portion is associated with the emitted light inciding on the element and the light detection element portion is associated with the back-scattered light scattered back from the element for detection.

Within the context of the present application, the term "back-scattered light scattered back from the element" may particularly denote light or a light signal which may be received subsequent to a light scattering incidence at or in the element. In particular, the scattering event may comprise light reflection at an element surface of the element and/or a light scattering or multiple light scattering at the element surface and/or within the element beneath the element surface.

The term "element portion" may particularly denote a point of the element or a region of the element of regular or irregular shape. In particular, the element portion may comprise an element surface portion of an element surface of the element.

The term "light indicative of the emitted light" may particularly denote (a fraction of) emitted light emitted by the light emitting unit, and/or light to be emitted by the light emitting unit.

The terms "unit" and/or "element" may particularly denote a component comprising one or more than one members.

According to the exemplary aspects of the invention, the sensor device and the method may employ information obtained by the Doppler effect of light scattering at the movable object, in order to determine a flow characteristic of the object being movable in the element. A light incidence element portion associated with the emitted light inciding on the element and a light detection element portion associated with the light scattered back from the element for detection purposes may be spatially separated from one another. Accordingly, the light scattered back from the light detection element portion towards a light detecting unit may comprise a high fraction of light propagating through the element and being scattered at a movable object in the element, but not light scattered back from the light incidence element portion.

Accordingly, a signal-to-noise ratio of the sensor device may be high, since the sensor device may comprise a high sensitivity respecting deeper layers of the element and thus an improved depth sensitivity.

Next, further exemplary embodiments of the sensor device for determining a flow characteristic of an object being movable in an element will be explained. However, these embodiments also apply to the method of determining a flow characteristic of an object being movable in an element.

In particular, the light emitting unit may be configured as a laser (light) unit configured for emitting laser light at infrared wavelengths, particularly between ≥about 780 nanometer (nm) and ≤about 980 nm, further particularly at about 850 nm. In particular, the latter wavelength range may be favorable in connection with determining a flow characteristic of blood of a skin, since the skin may be transparent at these light wavelengths, thereby enhancing the depth sensitivity of the sensor device. In particular, the latter effect may be even more pronounced for light of about 850 nm wavelength.

The light emitting unit and the light detecting unit may be integrally formed, and in particular as the laser (light) unit. In particular, the laser unit may allow the emitted light and the detected back-scattered light to interfere, in order to generate a (self) mixed light signal. Thus, the sensor device and the method may employ self-mixing interferometry for determining the flow characteristics of the object. In particular, the determining step of the method may be facilitated in that known mathematical algorithms associated with the principle of self-mixing interferometry may be used during the evaluation of the flow characteristic. Further, a constructive design of the sensor device may be significantly facilitated in that the sensor may comprise a low number of components. Further, manufacturing costs of the sensor device may be low.

The optical unit may comprise a light path separation element configured for separating a light path of the emitted light towards the light incidence element portion from a light path of the back-scattered light scattered back from the light detection element portion. Accordingly, a spatial separation of the light incidence element portion and the light detection element portion may be accomplished. Further, interference between the light scattered back from the light incidence element portion and light scattered back from the light detection element portion may be reduced or even eliminated, thereby increasing the accuracy of the determination of the flow characteristic.

In particular, the light path separation element may comprise or may be configured as a beam splitter.

The light path separation element may be configured as a polarizing beam splitter, and a polarization direction of the emitted light emitted by the light emitting unit may be oriented particularly under an angle of about 45 degrees with respect to a polarization axis of the polarizing beam splitter. Thus, a signal intensity of the back-scattered light may be high, since the beam splitter may reflect the entire emitted light. Further, the polarizing beam splitter may not transmit, but may absorb a fraction of the emitted light which may not be reflected by the beam splitter.

The optical unit may comprise a light redirecting element configured for redirecting the emitted light received from the light path separation element towards the light incidence element portion. Thus, an additional degree of freedom for spatially separating the light incidence element portion and the light detection element portion from one another may be accomplished. The usage of the light redirecting element may be particularly favorable in conjunction with the light path separation element comprising the beam splitter, since the light redirecting element may allow for redirecting the emitted light being reflected under an angle of about 90 degrees by the beam splitter element towards the element.

In particular, the light redirecting element may comprise or may be configured as a mirror and/or a prism. This measure may allow for a constructive easy embodiment of the light redirecting element.

A distance between the light incidence element portion and the light detection element portion may be adjustable by a relative arrangement of the light path separation element and the light redirecting element. Thus, the optical unit may provide a measure for selecting the depth information of the back-scattered light used for the determination of the flow characteristic, since the emitted light may propagate over a certain distance through the element and may be scattered at the movable object along this distance. In particular, in a case in which the light incidence element portion and the light detection element portion may be arranged close to one another, the scattered light will have dominantly scattered from near surface layers of the object. In a case, in which the light incidence element portion and the light detection element portion may be spatially separated by a longer distance, the scattered light will have passed through deeper layers of the object. In a case in which the light incidence element portion and the light detection element portion may be arranged far from one another, a signal intensity of the back-scattered light may be low, since, owing to multiple scattering events along the distance between the light incidence element portion and the light detection element portion, only a low fraction of the emitted light propagating through the element may be scattered back towards the light detecting unit. Accordingly, the sensor device may comprise an adjustable depth sensitivity.

The light path separation element and the light redirecting element may be integrally formed, whereby manufacturing costs of the optical element and thus of the sensor device may be low. Further, by integrally forming the light path separation element and the light redirecting element miniaturization and mass production of the optical unit may be accomplished. Further, the optical unit may comprise a compact, small, and constructively easy design. Further, a determining accuracy may be increased, since timely induced optical misalignment between the light path separation element and the light redirecting element may be avoided.

In particular, the beam splitter of the light path separation element may comprise a rectangularly trapezoid-like formed cross section when seen along a light propagation path, wherein the light redirecting element may be configured as a reflecting layer of an inner surface on a side face of the beam splitter. Here, the term "rectangular trapezoid" may particularly denote a trapezoid comprising at least one rectangular angle between two sides of adjacent sides of the trapezoid. In particular, the rectangular trapezoid cross-section of the beam splitter may comprise two rectangular angles arranged next to one another when seen along a circumference of the trapezoid. In particular, the right angles of the trapezoid may be arranged adjacent to the light detection element portion, and the side face comprising the reflecting layer may be arranged adjacent to the light incidence element portion. Thus, the optical unit may comprise a standard component, namely the beam splitter, which may comprise first and second glass members particularly being glued together. Therefore the beam splitter may comprise a slight modification in comparison to a standard cubed beam splitter, thereby causing low manufacturing costs.

Alternatively, the light path separation element and the light redirecting element may be configured in a two-pieced way. In particular, the light path separation element may be configured as a cubed beam splitter, and the light redirecting element may be configured as a mirror.

The sensor device may further comprise a polarization alternation element arranged between the optical unit and the element, wherein the polarization alternation element may be configured for altering a polarization of the emitted light received from the optical unit and a polarization of the back-scattered light scattered back from the element. Thus, the determination of the flow characteristic of the object in the element may be based on a selected polarization of the emitted light and the back-scattered light, thereby excluding non-relevant light information from the flow characteristic determination and thus increasing the accuracy of the determination.

In particular, the polarization alternation element may be configured as a polarizer, in particular as a quarter wave plate and/or a half wave plate.

In particular, the light emitting unit may be configured for emitting light comprising a linear polarization, wherein the polarization alternation element may be configured for altering the linear polarization of the emitted light into a (right or left) circular polarization, and may be configured for selecting a (right or left) circular polarization of depolarized back-scattered light and altering this circular polarization into a linear polarization.

In particular, the light emitting unit may be configured for emitting light comprising a (right or left) circular polarization, wherein the polarization alternation element may be configured for altering the circular polarization of the emitted light into a linear polarization, and may be configured for selecting a linear polarization of depolarized back-scattered light and altering this linear polarization into a (right or left) circular polarization.

The optical unit, particularly the polarizing beam splitter, and the polarization alternation element may be configured and may be arranged relative to one another such that a polarization (direction) of the back-scattered light detected by the light detecting unit and a polarization (direction) of the light indicative of the emitted light may be orthogonal to one another. The term "orthogonal polarizations" may particularly denote that respective polarization directions may be rotated with respect to one another by an angle of about 90 degrees. Thus, the light indicative of the emitted light and/or the emitted light may comprise orthogonal polarization directions. Accordingly, the depth sensitivity of the sensor device may be further enhanced, since the back-scattered light which may be selected for analysis may stem from deeper layers of the element. In particular, to this end, the polarization of the detected back-scattered light may be changed owing to multiple scattering events in the element when propagating between the light incidence element portion and the light detection element portion. Further, light being reflected at the light incidence element portion towards the light detecting unit may comprise a polarization almost identical to the polarization of the emitted light and may thus not be detected by the light detecting unit.

The sensor device may further comprise a first lens arranged between the optical unit, particularly the polarization alternation element, and the light incidence element portion, wherein the first lens may be configured for focusing the emitted light towards the light incidence element portion, and/or a second lens arranged between the optical unit, particularly the polarization alternation element, and the light detection element portion, wherein the second lens may be configured for focusing the back-scattered light scattered back from the light detection element portion particularly towards the optical unit. Accordingly, the first lens may allow for adjusting a spatial extension of the light incidence element portion, in order to adjust a light deposition level of the emitted light on the element. The second lens may allow for adjusting or increasing the signal intensity of the back-scattered light towards the light detecting unit. Thus, the accuracy of the determination may be further increased.

The sensor device may further comprise a first optical fiber arranged between the optical unit, particularly the polarization alternation element, and the light incidence element portion, wherein the first optical fiber may be configured for directing the emitted light from the optical unit towards the light incidence element portion, and/or a second optical fiber arranged between the optical unit, particularly the polarization alternation element, and the light detection element portion, wherein the second optical fiber may be configured for directing the back-scattered light from the light detection element portion towards the optical unit, particularly the polarization alternation element. Thus, signal losses owing to light diffusion between the optical unit, particularly the polarization alternation element, and the light incidence element portion and the light detection element portion, respectively, may be omitted such that a signal intensity of the back-scattered light may be increased. Accordingly, the accuracy of the determination of the flow characteristic of the liquid in the element may be significantly enhanced.

The sensor device may further comprise a third lens arranged between the light detecting unit and the optical unit, particularly the interfacing side faces of the first and second glass members of the beam splitter of the optical unit, wherein the third lens may be configured for focusing the back-scattered light towards the light detecting unit. Thus, a signal intensity of the back-scattered light reaching the light detecting unit may be increased, thereby increasing the accuracy of the determination of the flow characteristic of the object.

In particular, in a case in which the light emitting unit and the light detecting unit may be integrally formed, the third lens may also be configured for focusing the emitted light emitted from the light emitting unit towards the optical unit. Accordingly, the third lens may comprise respective shaped surfaces.

In particular, the determining unit may comprise or may be configured as a photodiode configured for detecting the (laser) light emitted by the light detecting unit. This measure may allow for easily detecting the (laser) light comprising the self mixed light signal using a conventional electronic element.

In particular, the laser unit may comprise a photodiode configured for detecting the self mixed light signal, and may be configured for outputting a respective (electronic) signal to the determination unit.

The flow characteristic of the object may comprise at least one of a flow velocity of the object and a flow direction of the object, and/or wherein the object may comprise a blood cell or more blood cells and the element may comprise a skin. Accordingly, the sensor device may be configured for determining the flow velocity and/or the flow direction of the blood using a Doppler shift of the frequency of the light scattered at the blood cell(s) of the blood of the skin. In particular, the sensor device may be usable for medical diagnosis, and may be configured as a blood flow sensor device.

DESCRIPTION OF THE DRAWINGS

These and other aspects of the invention will be apparent from and elucidated with reference to the embodiments described hereinafter.

DETAILED DESCRIPTION OF EMBODIMENTS

Figure 1:
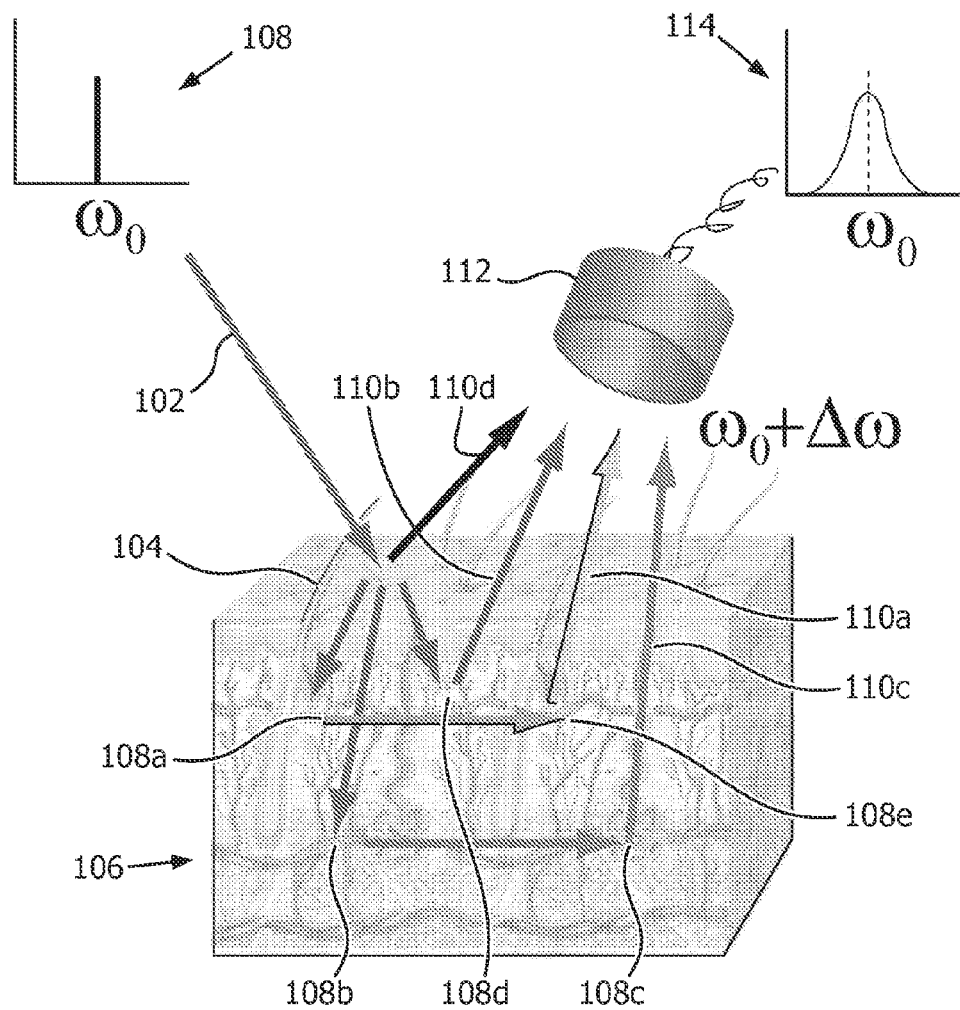
FIG. 1 is a schematic view of an arrangement for determining a flow characteristic of blood using LDF.
Figure 2:
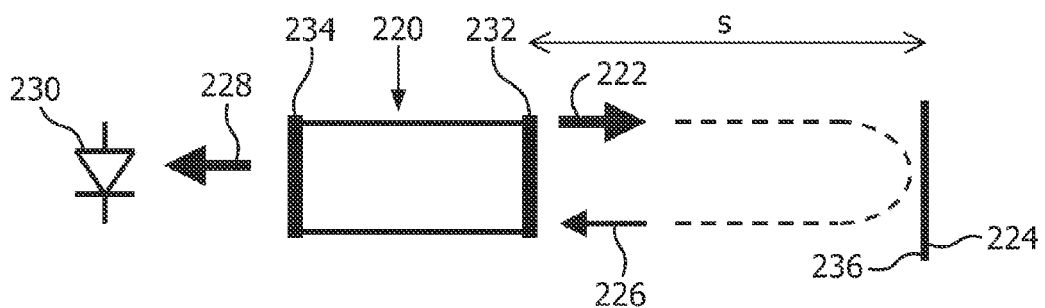
FIG. 2 is a schematic view of another arrangement for determining a flow characteristic of blood using SMI.

The invention in the drawing is schematic. It is noted that in different Figures, similar or identical elements are provided with the same reference signs or with reference signs, which are different from the respective reference signs only within a first digit.

Figure 3:
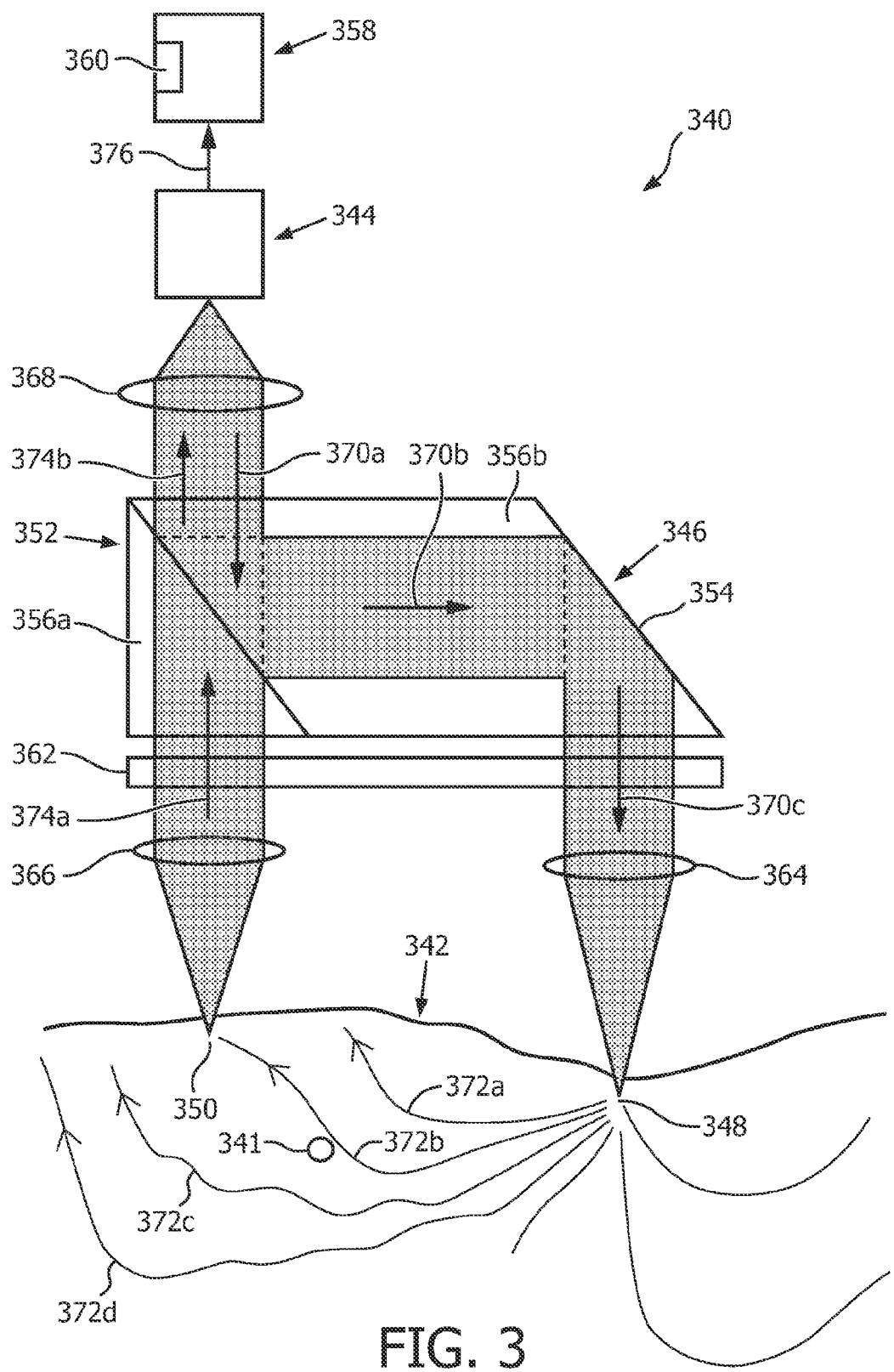
FIG. 3 is a schematic view of a sensor device for determining a flow characteristic of an object being movable in an element according to a first exemplary embodiment of the invention.

Referring to FIG. 3, a SMI based sensor device 340 for determining a flow characteristic of an object being movable in an element according to a first exemplary embodiment of the invention is illustrated. The sensor device 340 is used in the medical area for monitoring blood perfusion of a person by determining a flow velocity of blood cells 341 in a skin 342 of the person. For illustration purposes, a single blood cell 371 is schematically illustrated in FIG. 3. The sensor device 340 comprises an improved depth sensitivity and thus and an improved signal-to-noise ratio, since the sensor device 340 is sensitive to deeper layers of the skin 342 to be investigated.

The sensor device 340 comprises a light emitting and detecting unit 344 in the form of a laser unit configured for emitting coherent laser light of a linear polarization and for simultaneously detecting incoming (laser) light. The laser unit 340 operates at infrared wavelengths, particularly between 780 and 980 nm, for example at 850 nanometer (nm).

The sensor device 340 further comprises an optical unit 346 configured for spatially separating a light incidence skin portion 348 of the skin 342 associated with the emitted light inciding on the skin 342 and a light detection skin portion 350 of the skin 342 associated with light scattered back from the skin 342 for detection from one another. Each of the light incidence skin portion 348 and the light detection skin portion 350 are illustrated in FIG. 3 as a point, however, the light incidence skin portion 348 and/or the light detection skin portion 350 may be configured as a surface region having an irregular shape.

The optical unit 346 comprises a light path separation element 352 in the form of a polarizing beam splitter and a light redirecting element 354 in the form of a light reflecting element. The beam splitter 352 comprises a polarization axis aligned to a polarization direction of the linearly polarized emitted light under an angle of 45 degrees. The beam splitter 352 and the reflecting element 354 are integrally formed. The beam splitter 352 comprises a rectangularly trapezoid-like cross-section when seen along a light propagation direction of the emitted light through the beam splitter 352, and is made of first and second glass members 356a, b. The first glass member 356a comprises a triangle-like cross-section when seen along a light propagation direction of the emitted light through the first glass member 356a and a pyramidal-like three-dimensional shape, and the second glass member 356b comprises a trapezoid-like cross-section when seen along a light propagation direction through the second glass member 356b. The reflecting element 354 corresponds to an inner surface of a side face of the second glass member 356b of the beam splitter 352 which is arranged opposite to side faces of the first and second glass members 356a, b interfacing to one another. The light incidence skin portion 348 is located adjacent to the reflecting element 354, and the light detection skin portion 350 is located adjacent to the first glass member 356a of the polarizing beam splitter 352.

Further, the sensor device 340 comprises a determining unit 358 configured for determining the flow velocity of the blood cells 341 in the skin 342 based on a SMI signal generated in a cavity of the laser unit 344 by light indicative of the emitted light and the detected back-scattered light. To this end, the laser unit 344 is configured for outputting the laser light from a rear surface of the laser unit 344 towards the determining unit 358. The determining unit 358 comprises a photodiode 360 configured for detecting the laser light.

The sensor device 340 further comprises a polarization alternation element 362 arranged between the optical unit 346 and the skin 342 and being configured for altering a polarization of the emitted light received from the optical unit 346 and a polarization of the back-scattered light scattered back from the skin 342. The polarization alternation element 362 is configured as a quarter wave plate configured for altering a linear polarization of the emitted light passing through the quarter wave plate 362 to a circular polarization and for altering a circular polarization of the back-scattered light passing through the quarter wave plate 362 to a linear polarization.

The polarized beam splitter 352 and the quarter wave plate 362 are arranged to one another such that the linear polarization direction of the detected back-scattered light and the polarization direction of the emitted light are rotated to one another by 90 degrees.

First and second lenses 364, 366 are arranged between the quarter wave plate 362 and the light incidence skin portion 348 and the light detection skin portion 350 of the skin 342, respectively. The first lens 364 is configured for focusing the emitted light on the light incidence skin portion 348, and the second lens 366 is configured for focusing the back-scattered light towards the optical unit 346 by parallelly aligning light beams of the back-scattered light.

A third lens 368 of the sensor device 340 is arranged between the optical unit 346 and the laser unit 344, and is configured for focusing the back-scattered light to the laser unit 344 and for focusing the emitted light emitted from the laser unit 344 towards the optical unit 346 by parallelly aligning light beams of the emitted light.

Alternatively, the sensor device 340 may not comprise the first, second and third lenses 364, 366, 368. Signal quality losses owing to a non-presence of these components may be small, particularly when distances between the respective components of the sensor device 340 and the skin 342 may be small.

In operation of the sensor device 340, the laser unit 344 emits linearly polarized light towards the third lens 368 which in turn focuses the emitted light to be parallelly aligned. In FIG. 3, a propagation direction of the emitted light is indicated by arrows 370a-c, and a beam path of the emitted light is indicated in FIG. 3 in a dotted way, and is bordered by solid lines. The emitted light is then entirely reflected by the polarizing beam splitter 352 towards the reflecting layer 354. Subsequent to its reflection at the reflecting layer 354, the emitted light passes through the quarter wave plate 362 such that the linear polarization of the emitted light is altered into circular polarization. In the following, it will be assumed that the emitted light comprises a right circular polarization subsequent to passing the quarter wave plate 362. The emitted light is then focused by the first lens 364 towards the light incidence skin portion 348.

The emitted light incides on the light incidence skin portion 348, then propagates through surface layers of the skin 342, and scatters multiple times at the blood cells 371 along a light propagation path between the light incidence skin portion 348 and the light detection skin portion 350. Possible light propagation paths are indicated in FIG. 3 by arrows 372a-d. Accordingly, the emitted light is depolarized, hence comprises all possible polarizations.

The emitted light exits out of the surface of the skin 342 along the entire light propagation path between the light incidence skin portion 348 and the light detection skin portion 350. A fraction of the emitted light is scattered back from the light detection skin portion 350 towards the second lens 366 as back-scattered light. The second lens 366 collimates the back-scattered light towards the quarter wave plate 362 by parallelly aligning light beams of the back-scattered light. A propagation direction of the back-scattered light is indicated in FIG. 3 by arrows 372a, b. A beam path of the back-scattered light is indicated in FIG. 3 in a dotted way, and is bordered by solid lines. The quarter wave plate 362 selects a fraction of a left circular polarized back-scattered light out of the depolarized back-scattered light, and alters the left circularly polarized back-scattered light into linearly polarized back-scattered light. The back-scattered light then passes through the beam splitter 352 without any deflection or polarization change, and is collimated by the third lens 368 towards the laser unit 344. A fraction of right circular light of the depolarized emitted light may be altered by the quarter wave plate 362 into linear polarized light with the polarization direction being parallelly aligned with the polarization direction of the emitted light. This light fraction does not pass the polarizing beam splitter 352.

Within a cavity of the laser unit 344, the light to be emitted, which is indicative of the emitted light, and the detected back-scattered light received from the beam splitter 352 mix with one another such that self mixing interference occurs. The laser light is then outputted by the rear side of the laser unit 344 towards the determining unit 358. A propagation direction of the back side emitted laser light is indicated in FIG. 3 by an arrow 376. The photodiode 358 of the determining unit 358 detects the mixed light. The flow velocity of the blood cells 341 of the blood in the skin 342 of the person is determined based on the laser light detected by the photodiode 358.

It is noted that the quarter wave plate 362 in combination with the polarizing beam splitter 352 restricts the emitted light to be directly reflected at and/or back-scattered from the light incidence skin portion 348 towards the laser unit 344. This reflected and/or back-scattered light comprises—despite a reflection or scattering event—its original right circular polarization such that reflection of the accordingly linear polarized light, caused by its passage through the quarter wave plate 362, at the beam splitter 352 is prevented. Similarly, light reflected at the light incidence skin portion 348 towards the lens 366 does not enter the laser unit 344, since penetration of the accordingly polarized light through the beam splitter 352 is prevented owing to the polarization of the beam splitter 352.

Figure 4:
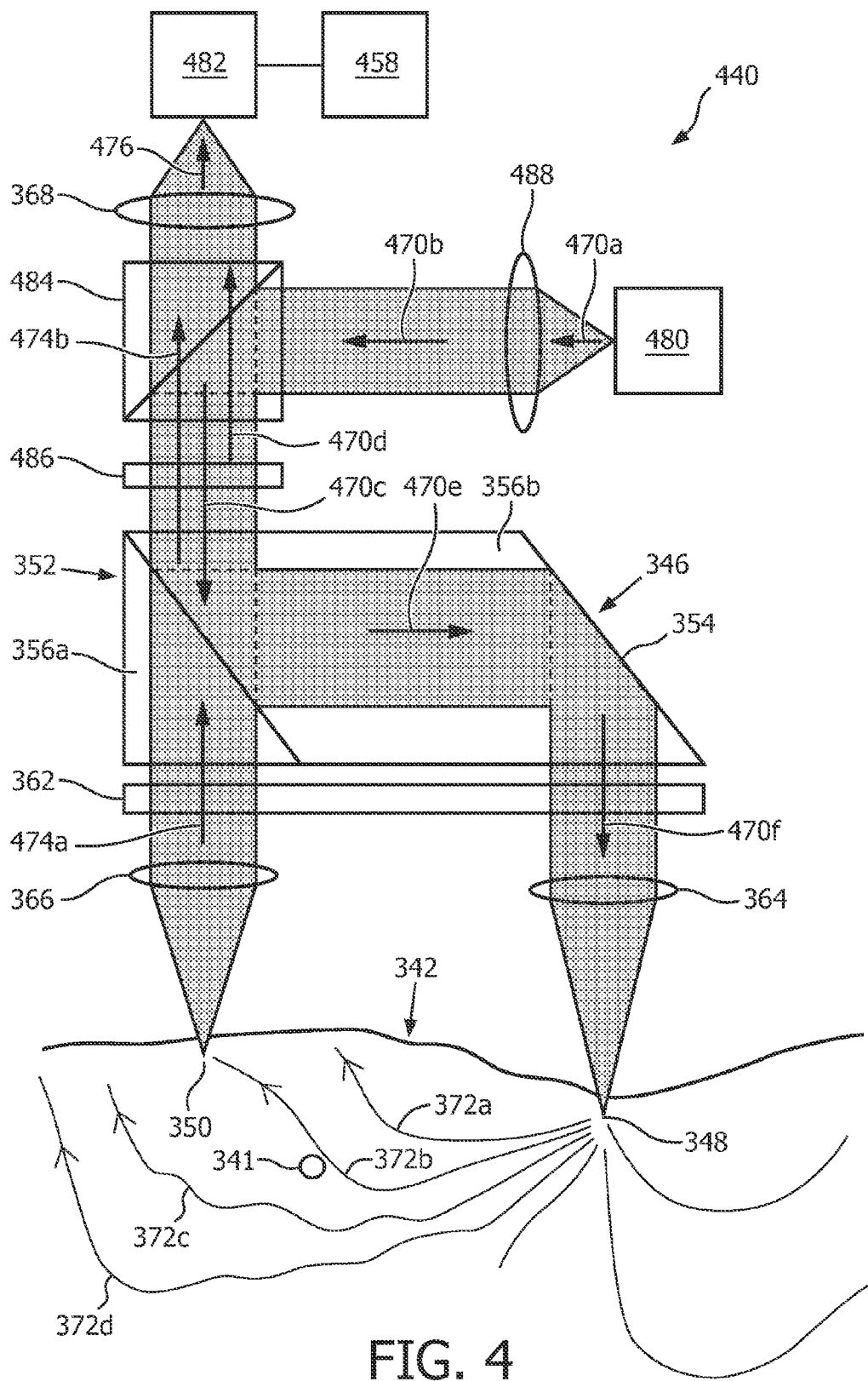
FIG. 4 is a schematic view of a sensor device for determining a flow characteristic of an object being movable in an element according to a second exemplary embodiment of the invention.

Referring to FIG. 4, a sensor device 440 according to a second exemplary embodiment of the invention will be explained. The sensor device 440 employs an interferometer arrangement, however, does not operate based on a principle of self-mixing interferometry. The sensor device 444 is similarly constructed compared to the sensor device 340 illustrated in FIG. 3, however, the sensor device 440 comprises a light emitting unit 480 and a light detecting unit 482 being configured as separate units. The light emitting unit 480 is configured as a laser diode configured for emitting coherent laser light of infrared wavelengths (here of 770 nm) and linear polarization, and the light detecting unit 482 is configured as a photodiode. Further, another polarizing beam splitter 484 is arranged between the laser diode 480 and the optical unit 346 and between the photodiode 482 and optical unit 346, respectively. The another polarizing beam splitter 484 is configured for reflecting the entire emitted light received from the laser diode 480 towards the beam splitter 352. Further, the polarizing beam splitter 362 and the another polarizing beam splitter 484 are configured and are arranged relative to one another that light received from the beam splitter 352 passes the beam splitter 484 without any deflection or change in polarization. A third lens 368 is arranged between the beam splitter 484 and the photodiode 484. An oscillating semi-reflecting plate 486 is arranged between the beam splitters 352, 484, and is configured for reflecting a fraction of the incoming emitted light received from the beam splitter 484 towards the photodiode 482 and for letting pass another fraction of the incoming emitted light towards the beam splitter 352. A fourth lens 488 is arranged between the laser diode 480 and the beam splitter 484, and is configured for focusing the emitted light to the beam splitter 484 by parallelly aligning light beams of the emitted light. The determining unit 458 comprises an identical functionality as to the flow velocity evaluation compared to the determining unit 358, but does not comprise a photodiode.

In operation of the sensor device 440, the laser diode 480 emits the light which passes through the fourth lens 488 towards the beam splitter 484. A propagation direction of the emitted light is indicated in FIG. 4 by arrows 470a-f. A beam path of the emitted light is indicated in FIG. 4 in a dotted way, and is bordered by solid lines. The beam splitter 484 entirely reflects the emitted light towards the beam splitter 352. A fraction of the emitted light passes through the oscillating semi-reflecting plate 486 (as indicated by the arrow 470c), and another fraction is directly scattered into the photodiode 482 (as indicated by the arrow 470d). An operation of the optical unit 346, the quarter wave plate 362, and the first and second lenses 364, 366 is identical compared to respective components of the sensor device 340. Here, a propagation direction of the back-scattered light is indicated in FIG. 4 by arrows 474a, b. A beam path of the back-scattered light is indicated in FIG. 4 in a dotted way, and is bordered by solid lines. The back-scattered light passes through the oscillating reflecting wave plate 486 and the beam splitter 484, and is focused by the third lens 368 towards the photodiode 482. The reflected fraction of the emitted light and the back-scattered light mix along the light path between the beam splitter 484 and the photodiode 482 such that the mixed light is detected by the photodiode 482. A light path of the mixed light is indicated in FIG. 4 by an arrow 476. The determining unit 458 determines the flow velocity of the blood vessels 371 based on the mixed light signal 376. To this end, the determining unit 458 receives a respective electrical signal from the photodiode 482.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A sensor device for determining a flow characteristic of an object being movable in an element, the sensor device comprising:
    a light emitting unit configured for emitting light towards the element,
    a light detecting unit configured for detecting light scattered back from the element,
    an optical structure including a light incidence lens portion and a light detection lens portion, the light incidence lens portion and the light detection lens portion being displaced from one another, wherein the light incidence lens portion is configured to emit light incident on the a first portion of the element and the light detection lens portion is configured to receive back-scattered light which is scattered back from a second portion of the element for detection, the first and second element portions being separated from each other, wherein the optical structure blocks any back-scattered light received by the light incident lens portion, and
    a unit configured for receiving light indicative of the emitted light and the detected back-scattered light such that the flow charactistics of the moveable object are determinable by self-mixing interferometry.

2. The sensor device according to claim 1, wherein the light emitting unit and the light detecting unit are integrally formed.

3. The sensor device according to claim 1, wherein the optical unit comprises a light path separation element configured for separating a light path of the emitted light towards the light incidence element portion from a light path of the back-scattered light scattered back from the light detection element portion.

4. The sensor device according to claim 3, wherein the light path separation element is configured as a polarizing beam splitter, wherein a polarization direction of the emitted light emitted by the light emitting unit is oriented under an angle of 45 degrees with respect to a polarization axis of the polarizing beam splitter.

5. The sensor device according to claim 3, wherein the optical unit comprises a light redirecting element configured for redirecting the emitted light received from the light path separation element towards the light incidence element portion.

6. The sensor device according to claim 5, wherein a distance between the light incidence element portion and the light detection element portion is adjustable by a relative arrangement of the light path separation element and the light redirecting element.

7. The sensor device according to claim 1, the sensor device further comprising:
    a polarization alternation element arranged between the optical unit and the element, wherein the polarization alternation element is configured for altering a polarization of the emitted light received from the optical unit and a polarization of the back-scattered light scattered back from the element.

8. The sensor device according to claim 7, wherein the optical unit and the polarization alternation element are configured and are arranged relative to one another such that a polarization of the back-scattered light detected by the light detecting unit and a polarization of the light indicative of the emitted light are orthogonal to one another.

9. The sensor device according to claim 1, the sensor device further comprising:
   a first lens arranged between the optical unit and the light incidence element portion, wherein the first lens is configured for focusing the emitted light towards the light incidence element portion, and/or
   a second lens arranged between the optical unit and the light detection element portion, wherein the second lens is configured for focusing the back-scattered light scattered back from the light detection element portion.

10. The sensor device according to claim 1, the sensor device further comprising:
    a first optical fiber arranged between the optical unit and the light incidence element portion, wherein the first optical fiber is configured for directing the emitted light from the optical unit towards the light incidence element portion, and/or
    a second optical fiber arranged between the optical unit and the light detection element portion, wherein the second optical fiber is configured for directing the back-scattered light from the light detection element portion to the optical unit.

11. The sensor device according to claim 1, the sensor device further comprising:
    a third lens arranged between the light detecting unit and the optical unit, wherein the third lens is configured for focusing the back-scattered light towards the light detecting unit.

12. The sensor device according to claim 1, wherein the flow characteristic of the object comprises at least one of a flow velocity of the object and a flow direction of the object, and/or wherein the object comprises a blood cell and the element comprises a skin.

13. A method of determining a flow characteristic of an object being movable in an element, the method comprising:
    emitting light towards the element by a light source,
    detecting light scattered back from the element by a light detector, and
    receiving light indicative of the emitted light and the detected back-scattered light with a unit to enable the flow characteristics of the moveable object to be determined by self-mixing interferometry,
    wherein a light incidence element portion of the element and a light detection element portion of the element are spatially separated from one another by an optical structure, wherein the optical structure channels emitted light from the light source to the light incidence element portion, channels backscattered light from the light detection element portion to the receiving unit, and prevents back-scattered light from the incident element portion from reaching the determining unit.

14. The method of claim 13, further comprising:
    separating a light path of the emitted light towards the light incidence element portion from a light path of the back-scattered light scattered back from the light detection element portion with a light path separation element.

15. The method of claim 14, further comprising:
    redirecting the emitted light received from the light path separation element towards the light incidence element portion with a light redirecting element; and
    adjusting a distance between the light incidence element portion and the light detection element portion by a relative arrangement of the light path separation element and the light redirecting element.

16. The method of claim 13, further comprising:
    altering a polarization of the emitted light received from the optical device and a polarization of the back-scattered light scattered back from the element with a polarization alternation element.

17. A sensor device for determining a flow characteristic of blood flowing in skin, the sensor device comprising:
    a light source;
    an optical element including:
        a light path separation element,
        a first optical element portion extending from adjacent the light source to the light path separation element,
        a second optical element portion extending from the light path separation element to a light output end adjacent an incident light region of the skin to receive incident light from the light source,
        a third optical element portion extending from a light receiving end adjacent another region of the skin displaced from the incident light region of the skin to receive backscattered light from the another region of the skin to convey the reeived backscattered light to the light path separation element;
    wherein the light separation element is configured to:
        pass light from the first optical element portion to the second optical element portion and block light from passing from the first optical element portion to the third optical element portion, and
        pass the backscattered light from the third optical element portion to the first optical element portion; and
    a means for determining a flow characteristic of the blood from backscattered light received from the third optical element portion and the light from the light source.

18. The sensor device according to claim 17, wherein the light path separation element includes a polarizing beam splitter.

19. The sensor device according to claim 18, further including:
    a polarizing plate disposed adjacent the outlet end of the second optical element portion, the polarizing plate and the polarizing beam splitter being polarized such that backscattered light from the incident light region of the skin is blocked from passing into the first optical element portion.

20. The sensor device according to claim 19, wherein the flow determining means includes an interferometer.

* * * * *